United States Patent [19]

Shneider et al.

[11] 4,129,126
[45] Dec. 12, 1978

[54] ORTHOPEDIC BRACE FOR USE IN TREATMENT OF LEGG PERTHES DISEASE

[76] Inventors: David Shneider, 4528 S. Hagadorn Rd., East Lansing, Mich. 48823; Lee D. Boerman, 1441 E. Michigan Ave., Lansing, Mich. 45912

[21] Appl. No.: 817,141

[22] Filed: Jul. 20, 1977

[51] Int. Cl.² .................................................. A61F 3/00
[52] U.S. Cl. ................................................... 128/80 A
[58] Field of Search ................... 128/80 A, 80 R, 80 J, 128/87 R, 83

[56] References Cited

U.S. PATENT DOCUMENTS

| 2,963,020 | 12/1960 | Moran | 128/80 A |
|---|---|---|---|
| 3,109,424 | 11/1963 | Brachman | 128/80 A |
| 3,931,817 | 1/1976 | Infranca | 128/80 A |

Primary Examiner—John D. Yasko
Attorney, Agent, or Firm—Malcolm R. McKinnon

[57] ABSTRACT

An orthopedic brace particularly adapted for use in connection with prescribed treatment of Legg Perthes Disease in the hips of children, the brace being comprised of a pair of angularly disposed support plates having the general outline of a conventional shoe sole and to which a pair of shoes that fit the patient may be attached, the support plates being interconnected by a rigid transversely extending cross bar having a vertically offset portion intermediate the support plates, the brace being effective to maintain the hips of a child in abduction and internal rotation, each support plate including a pad rotatable with respect to such support plate and providing for relatively friction free rotatable contact between the associated support plate and the ground whereby the brace enables the patient to walk in a restricted manner and to ascend and descend stairs, each support plate also including a fixed pad means facilitating braking action by the patient wearing the brace.

10 Claims, 8 Drawing Figures

U.S. Patent  Dec. 12, 1978  4,129,126
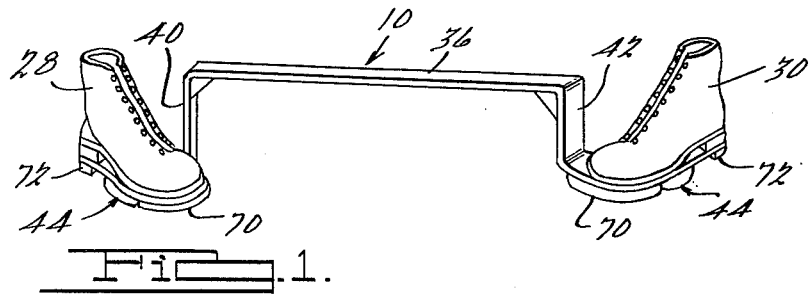
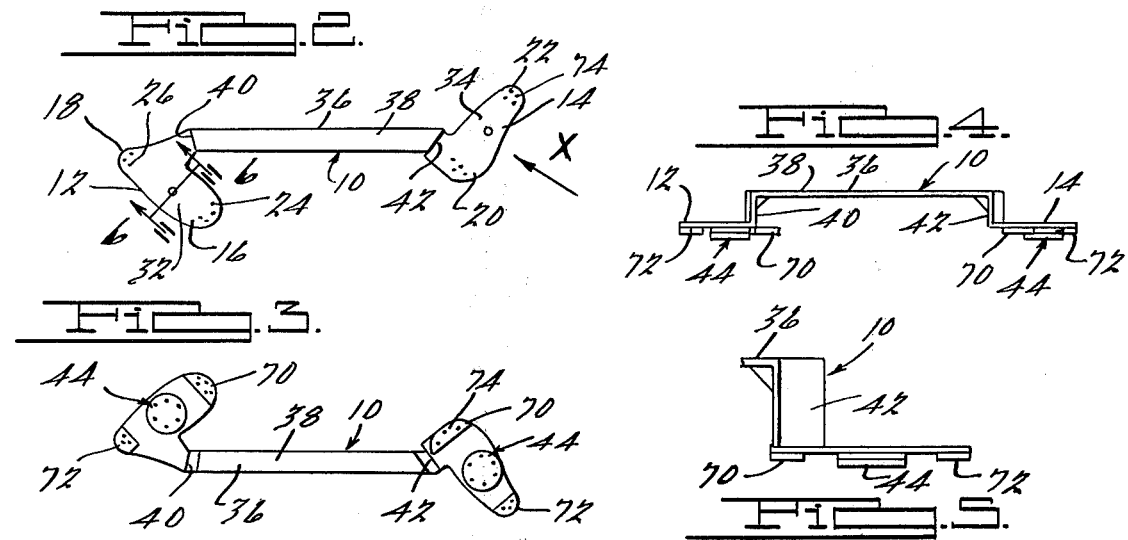
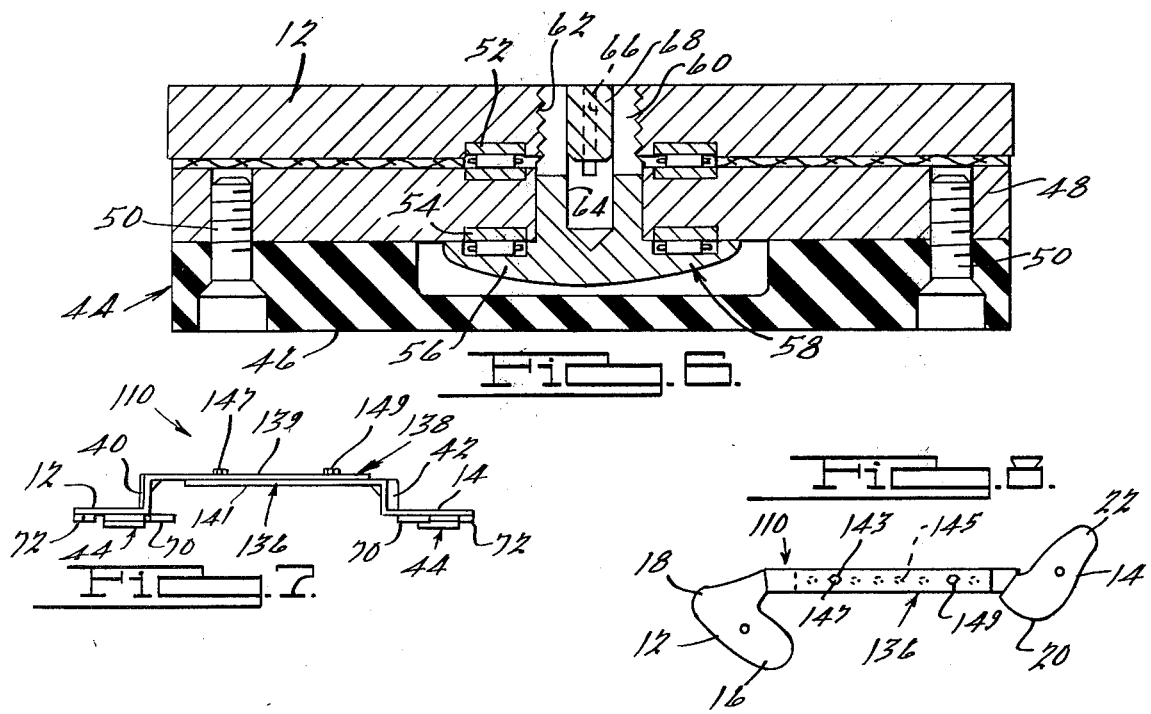

ORTHOPEDIC BRACE FOR USE IN TREATMENT OF LEGG PERTHES DISEASE

BRIEF SUMMARY OF THE INVENTION

This invention relates to orthopedic braces, and, more particularly, to an improved orthopedic brace particularly adapted for use in connection with the treatment of Legg Perthes Disease affecting the hips of children. While this invention is particularly adapted for use in the treatment of Legg Perthes Disease of the hips in children, it will be understood that the present invention may also be applicable to other uses.

As is well known in the art, previous treatments for Legg Perthes Disease have included casting with both legs of the patient being placed in a cast held in abduction and internal rotation by a cross bar extending between the casts. Such treatment places the legs and hips in abduction and internal rotation and holds the correct position but substantially immobilizes the patient. As is also well known in the art, heretofore orthopedic braces have been provided which include a cross bar attached to the shoes of infants and children in such a manner as to allow for adjustability in the positioning of the feet relative to the patient's body. Such braces are useful in correcting congenital disorders of the hips and feet, such as abnormal positioning and shape of the feet, known as clubfoot; inversion of the feet or rolling in of the soles so that the soles of the feet face each other; and an abduction of the forefoot, known as pigeon-toe deformity; and congenital dislocation of the hips as well as dysplasia problems. Heretofore, various orthopedic appliances such as the devices disclosed in U.S. Pat. Nos. 2,906,261; 2,963,020 and 3,523,526 have been proposed or utilized for the correction of the above mentioned diseases and/or deformities, with the intention of providing a brace allowing relative freedom of movement to the wearer during the lengthly treatment of such conditions. However, such prior art devices have not been adequately suited to the treatment of Legg Perthes Disease in children because of the inherent inability of such prior art devices to maintain proper internal rotation. Such prior devices also require very bulky, cumbersome braces and/or uprights on both legs merely to hold abduction without maintaining proper internal rotation. Furthermore, prior devices of the indicated character have been subject to a number of other deficiencies in that they are heavy, require frequent maintenance, are subject to frequent breakage, are very expensive to manufacture and maintain, and do not permit relatively free mobility of the wearer.

An object of the present invention is to overcome the aforementioned as well as other disadvantages in prior orthopedic braces of the indicated character and to provide an improved orthopedic brace incorporating improved means suited for the prescribed treatment of Legg Perthes Disease and allowing relatively free movement of the wearer during such treatment.

Another object of the invention is to provide an improved orthopedic brace for the treatment of Legg Perthes Disease which will maintain correct abduction and internal rotation to provide centralization of the femoral head in the acetabulum.

Another object of the present invention is to provide an improved orthopedic brace for the treatment of Legg Perthes Disease which may be easily and quickly mounted on and/or removed from the shoes of children by using a limited number of tools and a limited amount of effort.

Another object of the present invention is to enable the treatment of Legg Perthes Disease while permitting fitting of the brace to the specific treatment needs of the wearer.

Still another object of the present invention is to provide an improved orthopedic brace incorporating improved means providing relatively friction free rotatable contact between the bottom of the brace and the ground thereby permitting the wearer to continue near-normal walking activity levels during treatment of Legg Perthes Disease.

Still another object of the present invention is to provide an improved orthopedic brace which enables the patient wearing the brace to ascend and descend stairways and grades thereby enhancing the patient's mobility during treatment of Legg Perthes Disease.

Yet another object of the present invention is to provide an improved orthopedic brace for the treatment of Legg Perthes Disease which brace is light in weight and easily maneuverable by the wearer, economical to manufacture and assemble, durable, efficient and reliable in use.

The above as well as other objects and advantages of the present invention will become apparent from the following description, the appended claims and the accompanying drawings.

BRIEF DESCRIPTION OF THE DRAWINGS

FIG. 1 is a perspective view of an orthopedic brace embodying the present invention, and also illustrating the manner in which a patient's shoes may be attached to the brace;

FIG. 2 is a top plan view of the orthopedic brace illustrated in FIG. 1;

FIG. 3 is a bottom plan view of the orthopedic brace illustrated in FIG. 1;

FIG. 4 is a front elevational view of the orthopedic brace illustrated in FIG. 1;

FIG. 5 is an enlarged end view of a portion of the structure illustrated in FIG. 2 and looking in the direction of the arrow "X;"

FIG. 6 is an enlarged cross sectional view of a portion of the structure illustrated in FIG. 2, taken on the line 6—6 thereof;

FIG. 7 is a front elevational view of another embodiment of the invention; and

FIG. 8 is a top plan view of the structure illustrated in FIG. 7.

DETAILED DESCRIPTION

Referring to the drawings, an orthopedic brace, generally designated 10, embodying the present invention is illustrated in FIGS. 1 through 6 thereof, the orthopedic brace 10 being particularly adapted for use in connection with prescribed treatment of Legg Perthes Disease in the hips of children. The orthopedic brace 10 is preferably made of aluminum or other relatively lightweight material having sufficient strength to withstand the forces exerted thereon, and is comprised of a pair of angularly disposed support plates 12 and 14 each having the general outline of a conventional shoe sole, the support plate 12 having a toe portion 16 and a heel portion 18 while the support plate 14 includes a toe portion 20 and a heel portion 22. The toe and heel portions of each of the support plates are provided with internally threaded openings, such as 24 and 26, adapted to receive screws or rivets (not shown) passing through the toe and heel portions of the patient's shoes whereby the patient's shoes, such as 28 and 30, may be firmly secured to the upper surfaces 32 and 34, respectively, of the support plates 14 and 14. The support plates 12 and 14 are interconnected by a rigid, transversely extending cross bar 36 of generally inverted U-shaped configuration, the cross bar 36 including a vertically offset, horizontally extending central portion 38 integrally joined to a pair of spaced vertically extending flange portions 40 and 42. The flange portion 40 is fixed to the heel portion 18 of the support plate 12 while the flange portion 42 is fixed to the toe portion 20 of the support plate 14 so that the vertically offset portion 38 extends between the heel portion 18 of the support plate 12 and the toe portion 20 of the support plate 14. By way of illustration, the vertically offset central portion 38 of the cross bar may be offset approximately six inches from the plane of the upper surfaces 32 and 34 of the support plates 12 and 14 respectively. Such a construction enables the patient to ascend and descend stairways by providing clearance for the cross bar 36 to pass over the riser and tread of each stair as the patient swings first one support plate and then the other support plate up or down the stairs.

As previously mentioned, the support plates 12 and 14 are angularly disposed with respect to each other, the support plates 12 and 14 preferably being angularly disposed in a manner such that the longitudinal axes passing through the toe and heel portions of the support plates intersect at an angle of approximately ninety degrees. Such a construction is effective to hold the desired position of the femoral head in the acetabulum and maintain the hips of a child in abduction and internal rotation.

A rotatable pad 44 is secured to the central portion of the lower surface of each of the support plates 12 and 14 as shown in the drawings. Each rotatable pad 44 is comprised of a substantially circular ground engaging member 46 which may be formed of rubber, leather or other suitable sole type material, the member 46 being secured to a rotatable bearing plate 48 through the agency of screws 50. A pair of spaced bearings 52 and 54 are provided, the bearing 54 being disposed between the head portion 56 of a retaining member generally designated 58 and the bearing plate 48, while the bearing 52 is disposed between the bearing plate 48 and the support plate 12 or 14. The retaining member 58 also includes an externally threaded shank portion 60 adapted to threadably engage an opening 62 provided in the support plates 12 and 14. As shown in FIG. 6, the shank portion 60 of the retaining member 58 defines a centrally disposed blind passageway 64 having angularly disposed slots 66 communicating therewith, the passageway 64 being adapted to receive a tapered locking member 68 which functions to expand the externally threaded portion of the retaining member 58 into locking engagement with the associated support plate 12 or 14. With such a construction, the rotatable pads 46 provide relatively friction free rotatable contact between the associated support plate and the gound whereby the patient may alternately swing each support plate in an arc about the longitudinal axis of the rotatable pad on the other support plate so as to walk in a restricted manner while the patient's hips are maintained in abduction and internal rotation in the correct position.

The lower surfaces of each of the support plates 12 and 14 are provided with toe and heel pads 70 and 72 which are fixed to the toe and heel portions, respectively, of the support plates, as by screws 74. In the alternative, the pads may be cemented to the support plates. The ground engaging surfaces of the toe and heel pads 70 and 72 are preferably disposed in a plane approximately one-fourth inch above the plane of the ground engaging surface of the rotatable pad 44. With such a construction, the patient may tip either support plate 12 or 14 slightly so that either the toe or heel pads provide a braking action to halt the angular movement of the rotatable pad 44 and also provide a stable platform when the patient is in a standing rest position.

The usage of the orthopedic brace 10 is preferably confined to the ongoing treatment of Legg Perthes Disease in the hips of children. Thus, the orthopedic brace 10 is preferably used after a short period of casting to obtain the necessary internal rotation and the desired position of the femoral head in the acetabulum, after which the shoes of the patient may be fixed to the brace in the manner previously described whereby the child is enabled to walk in a restricted manner and to ascend and descend stairs in a restricted manner, thus permitting the patient to continue near-normal walking activity and enhancing the patient's mobility during the treatment of Legg Perthes Disease.

Another embodiment of the invention is illustrated in FIGS. 7 and 8 and is generally designated 110. This embodiment of the invention includes the support plates 12 and 14, the rotatable pads 44 and the toe and heel pads 70 and 72 all as previously described. However, in this embodiment of the invention, the mid portion 138 of the cross bar 136 is comprised of overlapping bars 139 and 141 having selectively alignable openings such as 143 in the bar 139 and internally threaded openings 145 in the bar 141 whereby the length of the mid portion of the cross bar may be adjusted and held in the selected adjusted position through the agency of bolts such as 147 and 149 which pass through the selected openings 143 in the bar 139 and threadably engage the internally threaded openings 145 in the bar 141. This embodiment of the invention operates in the same manner and produces the same results as the embodiment of athe invention illustrated in FIGS. 1 through 6 and described hereinabove.

While preferred embodiments of the invention have been illustrated and described, it will be understood that various changes and modifications may be made without departing from the spirit of the invention.

What is claimed is:

1. An orthopedic brace comprising, in combination, a pair of angularly disposed support plates, a rigid cross bar extending transversely between said support plates, a rotatable pad rotatably secured to the lower surface of each of said support plates, and fixed pad means secured to the lower surface of each of said support plates in spaced relationship with respect to said rotatable pad.

2. The combination as set forth in claim 1, said cross bar having a vertically offset portion intermediate said support plates.

3. The combination as set forth in claim 1, each of said support plates having the general outline of a shoe sole and including a toe portion and a heel portion.

4. The combination as set forth in claim 3, said cross bar extending between the toe portion of one of said support plates and the heel portion of the other of said support plates.

5. An orthopedic brace for use in connection with prescribed treatment of Legg Perthes Disease in the hips of children, said brace comprising, in combination, a pair of angularly disposed support plates each having the general outline of a shoe sole and including a toe portion and a heel portion, means for securing one of a pair of shoes to each of said support plates, a rigid cross bar extending between and secured to the toe portion of one of said support plates and the heel portion of the other of said support plates, a rotatable pad secured to the lower surface of the central portion of each of said support plates, a pair of fixed pads secured to the lower surface of the toe and heel portions of each of said support plates in spaced relationship with respect to said rotatable pad, the lower surface of each of said fixed pads being disposed above the lower surface of said rotatable pad.

6. The combination as set forth in claim 5, said cross bar having a vertically offset portion intermediate said support plates.

7. The combination as set forth in claim 6 including means for adjusting the length of said vertically offset portion.

8. The combination as set forth in claim 5 including bearing means disposed between said rotatable pad and the lower surface of the support plate associated therewith.

9. The combination as set forth in claim 5, each of said support plates and said cross bar being formed of aluminum.

10. The combination as set forth in claim 5, said rotatable pad and each of said fixed pads being formed of shoe sole material.

* * * * *